(12) United States Patent
Stahl et al.

(10) Patent No.: US 11,540,557 B2
(45) Date of Patent: Jan. 3, 2023

(54) NICOTINE POUCH PRODUCT

(71) Applicant: Philip Morris Products S.A., Neuchatel (CH)

(72) Inventors: My Ly Lao Stahl, Vejle Ost (DK); Heidi Ziegler Bruun, Vejle Ost (DK); Bruno Provstgaard Nielsen, Vejle Ost (DK); Bine Hare Jakobsen, Ry (DK)

(73) Assignee: Philip Morris Products S.A., Neuchatel (CH)

( * ) Notice: Subject to any disclaimer, the term of this patent is extended or adjusted under 35 U.S.C. 154(b) by 281 days.

(21) Appl. No.: 16/894,143

(22) Filed: Jun. 5, 2020

(65) Prior Publication Data

US 2020/0383373 A1 Dec. 10, 2020

(30) Foreign Application Priority Data

| Jun. 7, 2019 | (DK) | PA201900698 |
| Sep. 30, 2019 | (DK) | PA201970610 |
| Sep. 30, 2019 | (DK) | PA201970611 |
| Sep. 30, 2019 | (DK) | PA201970612 |

(51) Int. Cl.
| A24B 15/16 | (2020.01) |
| A24B 13/00 | (2006.01) |
| A24B 15/32 | (2006.01) |
| A24B 15/40 | (2006.01) |
| A24B 15/42 | (2006.01) |
| A24B 15/30 | (2006.01) |
| A61K 9/00 | (2006.01) |
| A61K 31/465 | (2006.01) |
| A24B 15/38 | (2006.01) |

(52) U.S. Cl.
CPC ............. *A24B 15/16* (2013.01); *A24B 13/00* (2013.01); *A24B 15/302* (2013.01); *A24B 15/32* (2013.01); *A24B 15/385* (2013.01); *A24B 15/403* (2013.01); *A24B 15/42* (2013.01); *A61K 9/006* (2013.01); *A61K 9/009* (2013.01); *A61K 31/465* (2013.01)

(58) Field of Classification Search
None
See application file for complete search history.

(56) References Cited

U.S. PATENT DOCUMENTS

| 5,167,244 | A | 12/1992 | Kjerstad |
| 8,863,755 | B2 | 10/2014 | Zhuang et al. |
| 9,402,809 | B2 | 8/2016 | Axelsson et al. |
| 11,096,412 | B2 | 8/2021 | Stahl et al. |
| 2005/0034738 | A1 | 2/2005 | Whalen |
| 2005/0053665 | A1 | 3/2005 | Ek et al. |
| 2005/0061339 | A1* | 3/2005 | Hansson ............... A24B 13/00 131/352 |
| 2008/0302682 | A1 | 12/2008 | Engstrom et al. |
| 2011/0214681 | A1 | 9/2011 | Axelsson et al. |
| 2012/0247492 | A1 | 10/2012 | Kobal et al. |
| 2013/0108558 | A1 | 5/2013 | Andersen |
| 2013/0152953 | A1 | 6/2013 | Mua et al. |
| 2014/0017286 | A1* | 1/2014 | Nilsson ............... A61K 9/1652 514/343 |
| 2015/0020818 | A1 | 1/2015 | Gao et al. |
| 2015/0068545 | A1 | 3/2015 | Moldoveanu et al. |
| 2015/0096576 | A1 | 4/2015 | Gao et al. |
| 2016/0000140 | A1 | 1/2016 | Sebastian et al. |
| 2016/0165953 | A1 | 6/2016 | Goode, Jr. |
| 2016/0192703 | A1 | 7/2016 | Sebastian et al. |
| 2017/0318858 | A1 | 11/2017 | Hodin et al. |
| 2018/0271139 | A1 | 9/2018 | Aspgren et al. |
| 2019/0037909 | A1 | 2/2019 | Greenbaum et al. |
| 2020/0297024 | A1 | 9/2020 | Bodin |

FOREIGN PATENT DOCUMENTS

| CN | 107319629 A | 11/2017 |
| EP | 2692254 A1 | 2/2014 |
| EP | 3087852 A1 | 11/2016 |
| EP | 3491940 A1 | 6/2019 |
| GB | 673587 A | 6/1952 |
| NO | 20170683 A1 | 10/2018 |
| WO | 2007084587 A2 | 7/2007 |
| WO | 2007104573 A2 | 9/2007 |
| WO | 2008056135 A2 | 5/2008 |
| WO | 2009010881 A2 | 1/2009 |
| WO | 2010121619 A1 | 10/2010 |
| WO | 2012134380 A1 | 10/2012 |
| WO | 2013090366 A2 | 6/2013 |
| WO | 2013152918 A1 | 10/2013 |

(Continued)

OTHER PUBLICATIONS

Additional Search Report from Danish Patent and Trademark Office for Application No. PA 2019 70610 dated Jul. 30, 2020 (2 pages).
Additional Search Report from Danish Patent and Trademark Office for Application No. PA 2019 70612 dated Aug. 4, 2020 (2 pages).
International Search Report Application No. PCT/DK2020/050159; dated Aug. 12, 2020; 3 pages.
International Search Report Application No. PCT/DK2020/050160; dated Oct. 1, 2020; 3 pages.
International Search Report Application No. PCT/DK2020/050162; dated Oct. 2, 2020; 4 pages.
International Search Report Application No. PCT/DK2020/050163; dated Oct. 7, 2020; 4 pages.

(Continued)

*Primary Examiner* — Dennis R Cordray
(74) *Attorney, Agent, or Firm* — Oblon, McClelland, Maier & Neustadt, L.L.P.

(57) ABSTRACT

A nicotine pouched product is disclosed, the nicotine pouched product having a pouch composition and a pouch membrane enclosing the pouch composition, the pouch composition including at least one water-insoluble fiber, water in an amount of at least 15% by weight of the composition, and nicotine, wherein the pouch membrane comprises further nicotine in an amount of at least 15% by weight of a total content of nicotine in the pouched product.

20 Claims, No Drawings

(56) References Cited

FOREIGN PATENT DOCUMENTS

| WO | 2015052282 A1 | 4/2015 |
| WO | 2015067372 A1 | 5/2015 |
| WO | 2015193379 A1 | 12/2015 |
| WO | 2016083463 A1 | 6/2016 |
| WO | 2017153718 A1 | 9/2017 |
| WO | 2018011470 A1 | 1/2018 |
| WO | 2018126262 A2 | 7/2018 |
| WO | 2018147454 A1 | 11/2018 |
| WO | 2018197454 A1 | 11/2018 |
| WO | 2018233795 A1 | 12/2018 |
| WO | 2019115778 A1 | 6/2019 |
| WO | 2020157280 A1 | 8/2020 |

OTHER PUBLICATIONS

Seidenberg, Andrew B., Olalekan A. Ayo-Yusuf, and Vaughan W. Rees. "Characteristics of 'American Snus' and Swedish Snus Products for Sale in Massachusetts, USA." Nicotine and Tobacco Research 20.2 (2018): 262-266.
Search Report from Danish Patent and Trademark Office for Application No. PA 2019 00698 dated Dec. 4, 2019 (1 page).
Search Report from Danish Patent and Trademark Office for Application No. PA 2019 70610 dated Feb. 7, 2020 (2 pages).
Search Report from Danish Patent and Trademark Office for Application No. PA 2019 70611 dated Feb. 3, 2020 (2 pages).
Search Report from Danish Patent and Trademark Office for Application No. PA2019 70612 dated Feb. 7, 2020 (2 pages).
Wikipedia, "Sugar alcohol"; https://en.wikipedia.org/wiki/Sugar_alcohol; downloaded from Internet on Sep. 27, 2017.

* cited by examiner though may include when only a part of the nicotine is bound to an ion exchange resin, such as polacrilex resin.

NICOTINE POUCH PRODUCT

FIELD OF THE INVENTION

The invention relates to a nicotine pouch composition according to the claims.

BACKGROUND OF THE INVENTION

Delivery of nicotine by smoking has many well-known drawbacks, in particular health related problems, such as inclusion of carcinogenic substances.

However, tobacco substitutes also suffer from disadvantages, such as inadequate relief of cravings for the user.

It is an object of one embodiment of the present invention to provide a nicotine containing pouch, e.g. as a tobacco substitute, which may solve the above problems.

A further challenge in the prior art is that the desired release of nicotine should be attractive to the user of the pouch from a user perspective.

Yet at further challenge in relation to the prior art may be that pouches as delivery vehicle for nicotine may be somewhat costly and thereby impose restrictions on the way pouches are designed in order to keep manufacturing costs in check.

SUMMARY OF THE INVENTION

The invention relates to a nicotine pouched product comprising
  a pouch composition and
  a pouch membrane enclosing the pouch composition,
  the pouch composition comprising
    at least one water-insoluble fiber,
    water in an amount of at least 15% by weight of the composition, and
    nicotine,
  wherein the pouch membrane comprises further nicotine in an amount of at least 15% by weight of a total content of nicotine in the pouched product.

An advantage of the invention may be that a relatively fast release of nicotine is facilitated due to the inclusion of said further nicotine in the pouch membrane. Thereby, the pouched product releases both nicotine from the pouch composition but in addition thereto, nicotine is released from the pouch membrane itself. Thereby, the nicotine release is greatly improved over pouches containing nicotine only in the pouch composition.

In many conventional pouches, attention has typically been focused the total amount of nicotine released within a use period of 30 minutes or even 60 minutes. However, the nicotine craving relief would still not necessarily be optimal. Instead, by adding nicotine to the pouch membrane, the release of nicotine was increased, especially during the first minutes after initiation of use, thereby providing a very desirable nicotine release and craving relief. This advantage is obtained without requiring e.g. special modification of the pouch composition but is instead accomplished by carefully distributing the nicotine of the pouched product such that at least a part of it is located in the pouch membrane. Also, it is accomplished without necessitating an increase in the overall nicotine amount, as the nicotine dose may instead be distributed over the pouch composition and the pouch membrane.

A further advantage of the invention may be that by providing a combination the claimed water content with said at least one water-insoluble fiber, a very desirable mouth feel may be obtained without the use of tobacco. At the same time, having the claimed amounts of water may facilitated faster release, especially within the first few minutes of use.

Thus, it should be understood in the present context that the pouch membrane comprises an amount of nicotine, and wherein sad amount of nicotine in the pouch membrane is at least 15% by weight of the total content of nicotine in the pouched product.

Furthermore, the pouched product comprises nicotine both in the pouch composition and in the pouch membrane. Therefore, the nicotine of the pouched product comprises the nicotine of the pouch composition and the nicotine of the pouch membrane.

In an advantageous embodiment of the invention, said at least one water-insoluble fiber is provided as a powder and wherein said pouch membrane comprises at least one further water-insoluble fiber.

In an advantageous embodiment of the invention, at least 15% by weight of said total content of nicotine in the pouched product is released within a period of no more than 120 seconds upon oral administration.

In an embodiment of the invention, this is measured by positioning the pouched product into a reaction tube containing 10 mL of 0.02 M potassium dihydrogen phosphate-buffer (pH adjusted to 7.4) and removing the pouched product and determining a remaining part of the nicotine in the pouched product.

The above in vitro method is described in more details in example 5F.

In an advantageous embodiment of the invention, 15-40% by weight of said total content of nicotine in the pouched product is released within a period of no more than 120 seconds upon oral administration.

In an embodiment of the invention, the pouch composition is adapted to release at least 15% by weight of total content of nicotine in the pouched product within a period of 120 seconds, such as at least 20% by weight of the total content of nicotine in the pouched product, such as at least 30% by weight of the total content of nicotine in the pouched product, when provided in a pouch and exposed to the in vitro release experiment described in example 5F.

In an embodiment of the invention, the pouch composition is adapted to release 15-50% by weight of total content of nicotine in the pouched product within a period of 120 seconds, such as 20-45% by weight of the total content of nicotine in the pouched product, such as 30-40% by weight of the total content of nicotine in the pouched product, when provided in a pouch and exposed to the in vitro release experiment described in example 5F.

In an advantageous embodiment of the invention, the nicotine of the pouched product is selected from nicotine salts, free-base nicotine mixed with ion exchange resin, free-base nicotine in complex with ion exchange resin, free-base nicotine mixed with a water-soluble composition such as sugar alcohol or water-soluble fiber, the nicotine in association with a fatty acid, such as oleic acid, and any combinations thereof.

In an advantageous embodiment of the invention, the nicotine of the pouched product does not consist of nicotine chemically bound to a carrier, such as an ion exchange resin, such as polacrilex resin.

Thus, in the above embodiment, the nicotine of the pouched product may be taken from any sources, except exclusively from nicotine chemically bound to a carrier. Particularly, the above embodiment does not include when all nicotine is bound to an ion exchange resin, such as polacrilex resin. On the other hand, the above embodiment includes at least some nicotine, which may or may not be bound to a carrier, insofar that this binding is physical, not chemical.

In an advantageous embodiment of the invention, the nicotine of the pouched product does not consist of nicotine salt.

In an embodiment of the invention, the nicotine of the pouched product does not comprise nicotine salt.

In an embodiment of the invention, the nicotine of the pouched product does not comprise nicotine bitartrate.

In an embodiment of the invention, the nicotine of the pouched product does not consist of nicotine bitartrate.

In an advantageous embodiment of the invention, the nicotine of the pouched product is selected from nicotine salts, free-base nicotine mixed with ion exchange resin, free-base nicotine mixed with a water-soluble composition such as sugar alcohol or water-soluble fiber, the nicotine in association with a fatty acid, such as oleic acid, and any combinations thereof.

In an advantageous embodiment of the invention, the nicotine of the pouched product is free-base nicotine mixed with ion exchange resin.

In an embodiment of the invention, the nicotine of the pouched product comprises free-base nicotine mixed with ion exchange resin.

In an advantageous embodiment of the invention the free-base nicotine comprises free-base nicotine mixed with ion exchange resin in a weight ratio between the free-base nicotine and the ion exchange resin of 0.1 to 2.0, preferably from 0.5 to 2.0, and most preferred about 0.67 to 1.0.

Here, a weight ratio refers to the ratio of the mass of the first component divided by the mass of the second component. The term mixing ratio may also be used.

In an embodiment of the invention, the nicotine of the pouched product comprises or is a nicotine salt.

In an embodiment of the invention, the nicotine of the pouched product comprises or is free-base nicotine, such as free-base nicotine mixed with ion exchange resin.

In an advantageous embodiment of the invention, the pouch composition comprises sugar alcohol.

In an advantageous embodiment of the invention, the pouch composition comprises sugar alcohol in an amount of at least 1% by weight of the composition, such as at least 2% by weight of the composition, such as at least 5% by weight of the composition, such as at least 10% by weight of the composition.

In an embodiment of the invention, the pouch composition comprises sugar alcohol in an amount of 1 to 80% by weight of the composition, such as 2 to 70% by weight of the composition, such as 5 to 60% by weight of the composition, such as 10 to 50% by weight of the composition.

In an embodiment of the invention the pouch composition comprises sugar alcohol in an amount of 5 to 40% by weight of the composition, such as 5-30% by weight of the composition.

In an advantageous embodiment of the invention, said sugar alcohol is selected from the group consisting of sorbitol, erythritol, xylitol, lactitol, maltitol, mannitol, hydrogenated starch hydrolyzates, isomalt, or any combination thereof.

In an embodiment of the invention, the sugar alcohol comprises a DC (direct compressible) grade sugar alcohol.

In an embodiment of the invention, at least 50% by weight of the sugar alcohol is a DC (direct compressible) grade sugar alcohol.

In an embodiment of the invention the sugar alcohol comprises a non-DC (non-direct compressible) grade sugar alcohol.

In an advantageous embodiment of the invention, the pouched product comprises said pouch membrane in an amount of up to 20 percent by weight of said pouched product, such as in an amount of up to 15 percent by weight of said pouched product.

In an advantageous embodiment of the invention, the pouched product comprises said pouch membrane in an amount of 3-20 percent by weight of said pouched product, such as in an amount of 5-15 percent by weight of said pouched product.

In an advantageous embodiment of the invention, the pouch membrane comprises a non-woven material or a woven material.

In an advantageous embodiment of the invention, the pouch membrane comprises a non-woven membrane.

In an embodiment of the invention, the pouch membrane comprises a woven membrane.

In an embodiment of the invention, the pouch membrane comprises a rayon fiber, such as viscose.

In an embodiment of the invention the fibers of the pouch membrane comprising cellulose in an amount of at least 60% by weight of the fibers, such as at least 80% by weight of the fibers.

In an embodiment of the invention, pouch membrane comprises fibers, the fibers of the pouch membrane comprising cellulose in an amount of 60-100% by weight of the fibers, such as 80-100% by weight of the fibers.

In an embodiment of the invention, the fibers of the pouch membrane consist essentially of cellulose.

In the present context, cellulose includes both natural cellulose, i.e. unmodified cellulose, and e.g. regenerated cellulose, such as rayon fibers.

Having a high content of cellulose may facilitate a fast release of nicotine from the pouch product.

In an embodiment of the invention, pouch membrane comprises fibers, the fibers of the pouch membrane comprising regenerated cellulose in an amount of at least 60% by weight of the fibers, such as at least 80% by weight of the fibers.

In an embodiment of the invention, pouch membrane comprises fibers, the fibers of the pouch membrane comprising regenerated cellulose in an amount of 60-100% by weight of the fibers, such as 80-100% by weight of the fibers.

In an embodiment of the invention, pouch membrane comprises fibers, the fibers of the pouch membrane comprising rayon in an amount of at least 60% by weight of the fibers, such as at least 80% by weight of the fibers. The rayon may e.g. comprise or consist of viscose.

In an embodiment of the invention, pouch membrane comprises fibers, the fibers of the pouch membrane comprising rayon in an amount of 60-100% by weight of the fibers, such as 80-100% by weight of the fibers. The rayon may e.g. comprise or consist of viscose.

In an embodiment of the invention, the fibers of the pouch membrane are natural.

In an embodiment of the invention, the fibers of the pouch membrane are free of synthetic fibers.

In an embodiment of the invention the pouch membrane is uncoated.

In an embodiment of the invention, the pouch membrane is free of synthetic coatings.

In an embodiment of the invention the pouch membrane comprises a coating, such as a non-fibrous coating.

In an advantageous embodiment of the invention, the amount of nicotine located in the pouch membrane is 15-50% by weight of said total content of nicotine in the pouched product, such as 15-35% by weight of said total content of nicotine in the pouched product.

In an embodiment of the invention, the amount of nicotine located in the pouch membrane is 15-45% by weight of said total content of nicotine in the pouched product.

In an embodiment of the invention, the amount of nicotine located in the pouch membrane is 15-40% by weight of said total content of nicotine in the pouched product.

In an embodiment of the invention, the amount of nicotine located in the pouch membrane is 15-30% by weight of said total content of nicotine in the pouched product.

In an embodiment of the invention, the amount of nicotine located in the pouch membrane is 20-50% by weight of said total content of nicotine in the pouched product, such as 25-50% by weight of said total content of nicotine in the pouched product, such as 30-50% by weight of said total content of nicotine in the pouched product.

In an advantageous embodiment of the invention, said amount of nicotine located in the pouch membrane is at least 20% by weight of a total content of nicotine in the pouched product, such as at least 25% by weight of a total content of nicotine in the pouched product.

In an advantageous embodiment of the invention, said amount of nicotine located in the pouch membrane is 20-50% by weight of a total content of nicotine in the pouched product, such as at least 25-50% by weight of a total content of nicotine in the pouched product.

In an advantageous embodiment of the invention, the further nicotine in the pouch membrane is provided by processing nicotine from the pouch composition into the pouch membrane.

In an embodiment of the invention, the processing of nicotine from the pouch composition into the pouch membrane may include subjecting the pouched product to predefined temperature and humidity.

In an embodiment of the invention, the nicotine in the pouch membrane is applied to the pouch membrane by a nicotine dispenser.

In an advantageous embodiment of the invention, the nicotine in the pouch membrane is applied to the pouch membrane by film coating or spraying.

In an advantageous embodiment of the invention, the nicotine in the pouch membrane is applied to the pouch membrane by soaking the pouched product in liquid nicotine, such as diluted liquid nicotine.

In an embodiment of the invention, the nicotine in the pouch membrane is applied to the pouch membrane before filling the pouch membrane with the pouch composition.

In an advantageous embodiment of the invention, further nicotine is applied to the pouch membrane during manufacturing of said pouch membrane.

In an advantageous embodiment of the invention, the nicotine in the pouch composition is the same form as the further nicotine in the pouch membrane.

In an advantageous embodiment of the invention, the pouch composition has a water content of 15 to 70% by weight of said pouch composition, such as 15 to 65% by weight of said pouch composition, such as 15 to 50% by weight of said pouch composition, such as 25 to 50% by weight of said pouch composition, such as 30 to 40% by weight of said pouch composition.

In an advantageous embodiment of the invention, the pouch composition has a water content of 15 to 70% by weight of said pouch composition, such as 15 to 50% by weight of said pouch composition, such as 15 to 40% by weight of said pouch composition, such as 15 to 30% by weight of said pouch composition, such as 15 to 25% by weight of said pouch composition.

The water may be added as a separate component of be fully or partly mixed into other components, such as fibers. E.g. when adding free-base nicotine as a mixture of free-base nicotine with ion exchange resin and water, a significant amount of water of the final pouch composition may come from the free-base nicotine-ion exchange resin-water pre-mixture. For example, if the final amount pouch composition comprises 5% water from free-base nicotine-ion exchange resin-water pre-mixture, then up to one third of the water in the pouch composition derives from the free-base nicotine-ion exchange resin-water pre-mixture.

In an advantageous embodiment of the invention, the pouch composition has a water content of no more than 60% by weight of said pouch composition, such as no more than 50% by weight of said pouch composition, such as no more than 40% by weight of said pouch composition, such as no more than 30% by weight of said pouch composition.

In an advantageous embodiment of the invention, the water-insoluble fiber of the pouch composition is selected from water-insoluble plant fiber, wheat fibers, pea fibers, rice fiber, maize fibers, oat fibers, tomato fibers, barley fibers, rye fibers, sugar beet fibers, buckwheat fibers, potato fibers, apple fibers, cocoa fibers, bamboo fibers, bran fibers, powdered cellulose, and any combination thereof.

Powdered cellulose within the scope of the invention is understood to be cellulose prepared by processing alpha-cellulose obtained as a pulp from strains of fibrous plant materials, such as wood pulp.

In an advantageous embodiment of the invention, the water-insoluble fiber of the pouch composition is selected from oat fibers, wheat fibers, pea fibers, powdered cellulose, and any combination thereof.

In an advantageous embodiment of the invention, the water-insoluble fibers comprise MCC.

In an advantageous embodiment of the invention, the water-insoluble fibers are powdered.

In an advantageous embodiment of the invention, the water-insoluble fiber of the pouch composition has a water binding capacity of at least 200%, such as at least 300%, such as at least 400%.

An advantage of the above embodiment may be that the high water-binding capacity enables pouch compositions having a high water-content.

In an embodiment of the invention, the water-insoluble fiber of the pouch composition has a water binding capacity of 200% to 1500%, such as 300 to 1300%, such as 200 to 800%, such as 300 to 800%, such as 400 to 600%.

In an embodiment of the invention, the water-insoluble fiber has a water binding capacity of 200 to 1500%, such as 300 to 1300%, such as 300 to 900%, such as 300 to 700%, such as 400 to 700%.

In an embodiment of the invention, the water-insoluble fiber has a water binding capacity of 200 to 1500%, such as 400 to 1500%, such as 500 to 1500%, such as 500 to 1200%, such as 500 to 1000%.

In an embodiment of the invention, the water-insoluble fiber has a swelling capacity of at least 5.0 mL/g, such as 5.0-20 mL/g.

An advantage of the above embodiment is that the amount of water-insoluble fiber can be reduced without compromising the mouthfeel during use. If an amount of water-insoluble fiber is substituted for a water-soluble component, the swelling of the water-insoluble fiber will during use counteract the dissolution of the water-soluble component, thereby the user will not experience any decrease in pouch content during use.

In an advantageous embodiment of the invention, the composition has a bulk density of at most 0.8 g/cm3, such as has a bulk density of at most 0.7 g/cm3, such as at most 0.6 g/cm3, such as at most 0.5 g/cm3.

The inventive use of a composition having a relatively low bulk density, will provide not only a good mouthfeel, but also an effective release from the pouch, due to the fact that a relatively low bulk density promotes effective salivation and thereby release of water-soluble ingredients of the composition. It is in particular noted that the low bulk density, in combination with the claimed water content, is attractive when improved user perception is desired.

At the same time, a low density advantageously lowers the need for raw materials and thereby decreases production costs.

An advantage of the above embodiment may be that a low-density composition may be obtained. Unexpectedly, the combination of water and sugar alcohols did not lead to a very dense, compact and un-processable pouch composition but allowed a relatively light and low-density composition.

In an advantageous embodiment of the invention, the pouch composition comprises water and water-insoluble fiber in a weight ratio of no more than 3.0, such as no more than 2.5, such as no more than 2.0, such as no more than 1.5, such as no more than 1.0.

In an advantageous embodiment of the invention, the pouch composition is free of tobacco, tobacco fibers and fibers derived from tobacco.

In some alternative embodiments, the pouch composition may comprise minor amounts of tobacco. Any, nicotine provided as part of tobacco, such as e.g. powdered tobacco, is further to the free-base nicotine. Such tobacco may e.g. be included to provide tobacco flavor.

In an embodiment, the pouch composition may comprise tobacco, tobacco fibers, or fibers derived from tobacco in an amount of 0.1 to 5.0% by weight of the pouch composition, such as in an amount of 0.1 to 3.0% by weight of the pouch composition. Thus, while the pouch composition in some embodiments may comprise small amounts of tobacco, this is in addition to the free-base nicotine, and thus the pouch composition is not tobacco based.

In an embodiment of the invention, the pouch composition comprises less than 5.0% by weight of tobacco, such as less than 3.0% by weight of the pouch composition, such as less than 1.0% by weight of the pouch composition, such as less than 0.5% by weight of the pouch composition, such as less than 0.1% by weight of the pouch composition, such as being free of tobacco.

In an embodiment of the invention, the water-insoluble composition does not comprise tobacco, tobacco fibers or fibers derived from tobacco. Thus, in this embodiment, the water-insoluble fibers are non-tobacco fibers, i.e. does not comprise tobacco, tobacco fibers, or fibers derived from tobacco.

In an embodiment of the invention the membrane comprises water insoluble fiber of different origin than the water insoluble fiber contained in the pouched product.

In an embodiment of the invention both the water insoluble fiber of the membrane and the water-insoluble fiber of the pouch composition comprises natural fiber.

In an embodiment of the invention both the water insoluble fibers of the membrane and the water-insoluble fibers of the pouch composition are natural fibers.

In an advantageous embodiment of the invention, the pouch composition said composition comprises sugar alcohol selected from the group consisting of sorbitol, erythritol, xylitol, lactitol, maltitol, mannitol, hydrogenated starch hydrolyzates, isomalt, or any combination thereof and wherein the composition comprises said sugar alcohol in an amount of 1-80% by weight of the pouch composition, such as 5-70% by weight of the pouch composition, such as 10-60% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, and wherein said composition further comprises water-insoluble fibers in an amount of between 5 and 50% by weight of the pouch composition, such as between 10 and 30% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and therein the water-insoluble composition comprises or consists of water-insoluble fiber, such as a water-insoluble plant fiber, such as wheat fibers, oat fibers, pea fibers, powdered cellulose, or combinations thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, wherein the water-insoluble composition comprises or consists of water-insoluble fiber, such as a water-insoluble plant fiber, such as wheat fibers, oat fibers, pea fibers, powdered cellulose, or combinations thereof and wherein the pouch composition comprises flavor in an amount between 0.01 and 15% by weight of the pouch composition, such as between 0.1 and 15% by weight of the pouch composition, such as between 1 and 10% by weight of the pouch composition, such as between 3 and 10% by weight of the pouch composition and wherein the flavor is oil-based.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potassium carbonate, Calcium carbonate, Magnesium carbonate, Magnesium oxide, or any combination thereof.

In an advantageous embodiment of the invention, said pouch composition comprises sugar alcohol selected from the group consisting of sorbitol, erythritol, xylitol, lactitol, maltitol, mannitol, hydrogenated starch hydrolyzates, isomalt, or any combination thereof, wherein the composition comprises said sugar alcohol in an amount of 1-80% by weight of the pouch composition, such as 5-70% by weight of the pouch composition, such as 10-60% by weight of the pouch composition, wherein said composition further comprises water-insoluble fibers in an amount of between 5 and 50% by weight of the pouch composition, such as between 10 and 30% by weight of the pouch composition, and wherein the pouch composition comprises a pH regulating agent which is a basic pH regulating agent, such as a basic buffering agent and/or such as Sodium carbonate, Sodium bicarbonate, Potassium carbonate, Potassium bicarbonate, Magnesium carbonate, or any combination thereof.

The invention relates in a second aspect to a nicotine pouched product comprising
  a pouch composition and
  a pouch membrane enclosing the pouch composition,
  the pouch composition comprising
    at least one water-insoluble fiber,
    water in an amount of at least 15% by weight of the composition and
    nicotine,
  wherein the pouch membrane further comprises at least 1.0 mg nicotine.

In an embodiment of the invention, the nicotine pouched product of the second aspect is devised in accordance with the first aspect of the invention or any of its embodiments.

DETAILED DESCRIPTION OF THE INVENTION

As used herein the term "nicotine" refers to nicotine used as a refined/isolated substance. Particularly, nicotine does not refer to tobacco materials having a content of nicotine.

As used herein the term "pouch composition" refers to the composition for use in a pouched product, i.e. in pouches for oral use comprising nicotine. Also, the terms "nicotine pouch composition" and "pouch composition" is used interchangeably. The pouch composition is not a tobacco-based pouch composition. In some embodiments, the pouch composition may comprise small amounts of tobacco e.g. as a flavoring, below 2% by weight of the composition. In other embodiments, the pouch composition is free of tobacco.

As used herein the term "free-base nicotine" refers to non-protonated form of nicotine, and therefore does not include nicotine salts and nicotine provided as a complex between nicotine and an ion exchange resin. Nevertheless, the free-base nicotine may be mixed with an amount of ion exchange resin or water-soluble compositions such as sugar alcohols or water-soluble fibers. Free-base nicotine may also be mixed with water-insoluble compositions, such as water-insoluble fiber. While free-base nicotine includes both free-base nicotine extracted from tobacco as well as synthetically manufactured free-base nicotine, the free-base nicotine is not provided in the form of tobacco or powdered tobacco. Typically, free-base nicotine is provided as a liquid.

As used herein the term "pouch membrane" is intended to refer to the material forming a container enclosing a cavity. The pouch membrane is designed for administration of nicotine in the oral cavity, and thus it is adapted for oral use, it is non-toxic and not water-soluble. The pouch membrane, which may be also be referred to as a web of a fibrous material, may e.g. form a woven or non-woven web or fabric. The pouched product may for example be sealed by bonding two corresponding pieces of web or fabric to each other along their edges to form a cavity for the nicotine and the water-insoluble composition. In order to release the nicotine, flavor, and other water-soluble substances, the pouch membrane is water-permeable so as to allow saliva from the oral cavity to penetrate the pouch membrane, where the saliva can come into contact with the nicotine, and also allow saliva to enter the cavity, where the saliva can come into contact with the nicotine, flavor, and other water-soluble substances, whereby the nicotine from the pouch membrane and the pouch composition, flavor and other water-soluble substances are released from the pouched product.

As used herein the term "powder composition" refers to composition in the form of powder, i.e. as a particulate material having a relatively small particle size, for example between 1 and 1200 micrometer. Particularly, by powder composition is not meant a powdered tobacco.

As used herein the term "humectant" is understood as a moistening agent used to attract moisture or water in the form of saliva. Humectants may typically include suitably hygroscopic compositions. In some cases, humectants may also be described as moistening agents, due to their role in attraction of moisture. Examples of humectants include glycerol, propylene glycol, alginate, pectin, xanthan gum, modified starch, hydroxypropyl cellulose, triacetin, polyethylene glycol (PEG), etc.

As used herein the term "water-soluble" refers to a relatively high water-solubility, for example a water-solubility of more than 5 gram of water-soluble composition or substance per 100 mL of water measured at 25 degrees Celsius and pH of 7.0. When referring to a "soluble" composition or substance, water-soluble is meant, unless otherwise stated.

As used herein the term "water-insoluble" refers to relatively low water-solubility, for example a water-solubility of less than 0.1 gram of water-soluble composition or substance per 100 mL of water measured at 25 degrees Celsius and pH of 7.0. When referring to "insoluble", water-insoluble is meant unless otherwise stated.

Typically, the pouch membrane comprise openings, where the characteristic opening dimension is adapted to a characteristic dimension of the pouch composition so as to retain the pouch composition inside the pouch before use and/or to retain a part of the pouch composition, such as an water-insoluble composition, inside the pouch during use.

In order to obtain a pouch membrane having suitable opening dimensions in view of the pouch composition to be used, the material for the pouch membrane may be selected accordingly, e.g. comprising e.g. woven and/or non-woven fabric.

In other words, according to the various embodiments, the pouch membrane allows passage of saliva and prevents or inhibits passage of undissolved composition and the water-insoluble fibers. The pouch membrane may be of any suitable material e.g. woven or non-woven fabric (e.g. cotton, fleece etc.), heat sealable non-woven cellulose, such as long fiber paper, or other polymeric materials such as a synthetic, semi-synthetic or natural polymeric material. An example of suitable material for the pouch membrane is paper made of pulp and a small amount of wet strength agent. A material suitable for use must provide a semi-permeable membrane layer to prevent the powder or composition from leaving the bag or pouch during use. Suitable materials are also those that do not have a significant impact on the release of nicotine from the pouch.

In more detail, regarding the material, the pouch membrane may be a natural, synthetic, semi-synthetic hydrophilic or hydrophobic membrane. It may be made from one or more biocompatible and physiologically acceptable polymeric material. Examples of suitable materials for the pouch membrane are cellulose acetate and derivatives thereof, carboxymethyl cellulose, polycellulose ester, other cellulose derivatives including ethylcellulose, propylcellulose, polyethylene, polypropylene, polystyrene, polyvinyl chloride, polyvinyl acetate, polymers of methacrylates and acrylates, natural rubber, polycarbonate, polyethylene terephthalate, polyester, polyamide and nylon. Other suitable materials are mentioned herein before.

Rayon fibers (i.e. regenerated cellulose), such as viscose rayon fibers may also be used, e.g. in combination with an acrylic polymer that acts as binder in the nonwoven material and provides for heat-sealing of the pouch membrane during manufacturing thereof. Other binders, such as one or more copolymers of vinyl acetate and acrylic acid ester, may also be used.

Suitable pouch membranes for are available under the trade names "taboka," CatchDry, Ettan, General, Granit, Goteborgs Rape, GrovSnus White, Metropol Kaktus, Mocca Anis, Mocca Mint, Mocca Wintergreen, Kicks, Probe, Prince, Skruf, TreAnkrare, Camel Snus Original, Camel Snus Frost and Camel Snus Spice. The pouch membrane provides a liquid-permeable container of a type that may be considered to be similar in character to the mesh-like type of material that is used for the construction of a tea bag. Desired components of the nicotine composition to be released diffuse through the pouch membrane and into the mouth of the user.

Materials of the pouch membrane may have the form of a mesh, screen, perforated paper, permeable fabric, or the like. For example, pouch material manufactured from a mesh-like form of rice paper, or perforated rice paper, may dissolve in the mouth of the user. In some exemplary embodiments, the materials of the pouch membrane may be manufactured using water dispersible film forming materials (e.g., binding agents such as alginates, carboxymethylcellulose, xanthan gum, pullulan, and the like), as well as those materials in combination with materials such as ground cellulosics (e.g., fine particle size wood pulp). Preferred pouch materials, though water dispersible or dissolvable, may be designed and manufactured such that under conditions of normal use, a significant amount of the nicotine contents permeates through the pouch material prior to the time that the pouch undergoes loss of its physical integrity. If desired, flavoring ingredients, disintegration aids, and other desired components, may be incorporated within, or applied to, the pouch material.

Examples of various types of pouch membrane materials set forth in U.S. Pat. No. 5,167,244 to Kjerstad. Fleece materials for use as pouch membranes are described e.g. in WO 2008/152469, GB 673,587, and EP 2 692 254, hereby incorporated by reference.

According to an embodiment of the invention, the pouch composition comprises one or more pH-regulating agent, such as a buffering agent.

In an embodiment of the invention, said pH-regulating agents are selected from the group consisting of Acetic acid, Adipic acid, Citric acid, Fumaric acid, Glucono-δ-lactone, Gluconic acid, Lactic acid, Malic acid, Maleic acid, Tartaric acid, Succinic acid, Propionic acid, Ascorbic acid, Phosphoric acid, Sodium orthophosphate, Potassium orthophosphate, Calcium orthophosphate, Sodium diphosphate, Potassium diphosphate, Calcium diphosphate, Pentasodium triphosphate, Pentapotassium triphosphate, Sodium polyphosphate, Potassium polyphosphate, Carbonic acid, Sodium carbonate, Sodium bicarbonate, Potasium carbonate, Calcium carbonate, Magnesium carbonate, Magnesium oxide, or any combination thereof.

In an embodiment of the invention, said pH-regulating agents is selected from Sodium carbonate, Sodium bicarbonate, Potassium carbonate, Calcium carbonate, Magnesium carbonate, and any combination thereof.

According to various embodiments of the invention, one or more sugar alcohols may be included in the pouched product as part of the pouch composition, e.g. as a sweetener, as a humectant, or as a carrier or part thereof. Suitable sugar alcohols include sugar alcohols selected from the group of sorbitol, erythritol, xylitol, lactitol, maltitol, mannitol, hydrogenated starch hydrolyzates, isomalt, or any combination thereof.

In an embodiment of the invention the pouch composition comprises high intensity sweetener.

Preferred high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

In an embodiment of the invention, the pouch composition comprises sugar and/or sugarless sweeteners, e.g. sugar alcohol.

In an embodiment of the invention, the pouch composition comprises sugar and/or sugarless sweeteners in the amount of 1.0 to about 80% by weight of the pouch composition, more typically constitute 5 to about 70% by weight of the pouch composition, and more commonly 10 to 30% by weight of the pouch composition or 5 to 25% by weight of the pouch composition. In some other embodiments, the sugar and/or sugarless sweeteners constitute 10 to 60% by weight of the pouch composition or 10-50% by weight of the pouch composition. Sugar and/or sugarless sweeteners may function both as a sweetener and also as a humectant. In some embodiments, inclusion of certain ingredients may limit the about amounts of sugar and/or sugarless sweeteners further. In some embodiments, the content of sugar and/or sugarless sweeteners in the pouch composition is no more than 20% by weight of the pouch composition, such as no more than 15% by weight of the pouch composition, such as no more than 10% by weight of the pouch composition, such as no more than 5% by weight of the pouch composition.

The sweeteners may often support the flavor profile of the pouch composition.

Sugar sweeteners generally include, but are not limited to saccharide-containing components commonly known in the art of pouches, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

The sweetener can be used in combination with sugarless sweeteners. Generally, sugarless sweeteners include components with sweetening characteristics but which are devoid of the commonly known sugars and comprise, but are not limited to, sugar alcohols, such as sorbitol, mannitol, xylitol, hydrogenated starch hydrolyzates, maltitol, isomalt, erythritol, lactitol and the like, alone or in combination. These sugarless sweeteners may also be included as a humectant.

In embodiments of the invention, the pouch composition further comprises water soluble fibers. Non-limiting examples of water-soluble fibers include inulin, polydextrose, and psyllium plant fibers. Other water-soluble dietary fibers may also be used.

In an embodiment of the invention the pouch composition comprises flavor. Flavor may typically be present in amounts between 0.01 and 15% by weight of the total composition of the pouch, such as between 0.01 and 5% by weight of the total composition. In an alternative embodiment the pouch composition may be free of flavor.

Non-exhaustive examples of flavors suitable in embodiments of the present invention are coconut, coffee, chocolate, vanilla, citrus such as grape fruit, orange, lime, bergamot, or lemon, menthol, liquorice, caramel aroma, honey aroma, peanut, walnut, cashew, hazelnut, almonds, pineapple, strawberry, raspberry, tropical fruits, cherries, cinnamon, peppermint, wintergreen, spearmint, eucalyptus, and mint, fruit essence such as from apple, pear, peach, strawberry, apricot, raspberry, cherry, pineapple, lemongrass, lime, chili (capsaicin), citrus, tobacco flavor, bergamot, and plum essence. The essential oils include peppermint, spearmint, menthol, eucalyptus, clove oil, bay oil, anise, thyme, cedar leaf oil, nutmeg, and oils of the fruits mentioned above.

In various embodiments of the invention, the pouch composition comprises a release controlling composition for controlling the release of the pouch composition and/or parts thereof, especially the nicotine.

The release controlling composition may, according to various embodiments, be selected from the group consisting of metallic stearates, modified calcium carbonate, triglycerides (e.g. hydrogenated vegetable oils, partially hydrogenated vegetable oils, and/or animal fats), polyethylene glycols, polyoxyethylene monostearates, animal fats, silicates, silicon dioxide, talc, magnesium stearates, calcium stearates, fumed silica, powdered hydrogenated cottonseed oils, emulsifiers, hydrogenated soya oil and mixtures thereof. Particularly, metallic stearates, such as magnesium stearate, may be advantageous.

The release controlling composition may be added to the pouch composition in various ways.

For example, the release controlling composition may be added by full powder mixture during the last few minutes of the final mixing.

Alternatively, the release controlling composition may be added after granulation steps on a granulation premix.

Still further, the release controlling composition may be added only as a fraction of the pouch composition so two different release profiles of nicotine are achieved. Even further two or more fractions of the pouch composition may comprise different amounts of the release controlling composition, if any, thereby providing a more complex and tailored release profile of nicotine.

The release controlling composition, such as magnesium stearate, may have a sealing effect and can be used to control the release of the nicotine and the solubility of the pouch.

EXAMPLES

Example 1A—Preparation of Pouches Designed for Administration of Nicotine

A pouch membrane is manufactured using a heat sealable non-woven cellulose, such as long fiber paper. The pouch membrane is heat sealed along its edges except for an opening in one end into an inner cavity formed by the pouch membrane.

The powdered pouch composition is filled into cavity formed by the pouch membrane and is maintained in the pouch by a sealing.

Pouches that are not in form of non-woven cellulose fabric may also be used according to the invention.

Example 1B—Preparation of Pouches Designed for Administration of Nicotine

A pouch membrane is manufactured using rayon fibers, such as viscose rayon staple fibers. The pouch membrane is heat sealed along its edges except for an opening in one end into an inner cavity formed by the pouch membrane.

The powdered pouch composition is filled into cavity formed by the pouch membrane and is maintained in the pouch by a sealing.

Example 2A—Nicotine Premix I—Resin

A Stephan mixer (vacuum premixing) was charged with water, and nicotine was weighed and added, the mixer was closed and stirred for 5 minutes. Then ion exchange resin Amberlite® IRP64 was weighed and added to the mixer. The mixer was closed and stirred for 10-60 minutes.

Thereby, a mixture of nicotine and cation exchange resin was produced from the constituents stated in the below table 1.

TABLE 1

Ingredients used to manufacture nicotine premix I.

| Constituent | Amount (kg) | Amount (%) |
|---|---|---|
| Nicotine | 1.0 | 5.7 |
| Water | 12.5 | 71.4 |
| Resin | 4.0 | 22.9 |
| Total | 17.5 | 100.0 |

Nicotine:resin ratio: 1:4 (0.25)
% water in obtained nicotine-resin composition: 71.4

Example 2B—Nicotine Premix II—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 2.

TABLE 2

Ingredients used to manufacture nicotine premix II.

| Constituent | Amount (kg) | Amount (%) |
|---|---|---|
| Nicotine | 1.08 | 13.2 |
| Water | 2.80 | 34.1 |
| Resin | 4.32 | 52.7 |
| Total | 8.20 | 100.0 |

Nicotine:resin ratio: 1:4 (0.25)
% water in obtained nicotine-resin composition: 34.1
The total process time was 20 minutes.

Example 2C—Nicotine Premix III—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 3.

TABLE 3

Ingredients used to manufacture nicotine premix III.

| Constituent | Amount (kg) | Amount (%) |
|---|---|---|
| Nicotine | 1.08 | 18.5 |
| Water | 0.44 | 7.5 |
| Resin | 4.32 | 74.0 |
| Total | 5.84 | 100.0 |

Nicotine:resin ratio: 1:4 (0.25)
% water in obtained nicotine-resin composition: 7.5
The total process time was 20 minutes.

Example 2D—Nicotine Premix IV—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally the mixer was stirred for further 5 minutes at high speed.

Thereby, a mixture of nicotine and cation exchange resin was produced from the constituents stated in the below table 4.

TABLE 4

Ingredients used to manufacture nicotine premix IV.

| Constituent | Amount (kg) | Amount (%) |
|---|---|---|
| Nicotine | 1.08 | 10.0 |
| Water | 5.40 | 50.0 |
| Resin | 4.32 | 40.0 |
| Total | 10.8 | 100.0 |

Nicotine:resin ratio: 1:4 (0.25)
% water in obtained nicotine-resin composition: 50.0
The total process time was 20 minutes.

Example 2E—Nicotine Premix V—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4A.

TABLE 4A

Ingredients used to manufacture nicotine premix V.

| Constituent | Amount (kg) | Amount (%) |
|---|---|---|
| Nicotine | 1.78 | 20.0 |
| Water | 2.80 | 31.5 |
| Resin | 4.32 | 48.5 |
| Total | 8.90 | 100.0 |

Nicotine:resin ratio: 1:2.43 (0.41)
% water in obtained nicotine-resin composition: 31.5
The total process time was 20 minutes.

Example 2F—Nicotine Premix VI—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4B.

TABLE 4B

Ingredients used to manufacture nicotine premix V.

| Constituent | Amount (kg) | Amount (%) |
|---|---|---|
| Nicotine | 3.05 | 30.0 |
| Water | 2.80 | 27.5 |
| Resin | 4.32 | 42.5 |
| Total | 10.17 | 100.0 |

Nicotine:resin ratio: 1:1.4 (0.71)
% water in obtained nicotine-resin composition: 27.5
The total process time was 20 minutes.

Example 2G—Nicotine Premix VII—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4C.

TABLE 4C

Ingredients used to manufacture nicotine premix V.

| Constituent | Amount (kg) | Amount (%) |
|---|---|---|
| Nicotine | 5.15 | 42.0 |
| Water | 2.80 | 22.8 |
| Resin | 4.32 | 35.2 |
| Total | 12.27 | 100.0 |

Nicotine:resin ratio: 1.19:1 (1.19)
% water in obtained nicotine-resin composition: 22.8
The total process time was 20 minutes.

Example 2H—Nicotine Premix VIII—Resin

A 60 liter planetary Bear Varimixer mixer was charged with water, and nicotine was weighed and added. The mixer was stirred at low speed for 1 minute at ambient temperature. Then ion exchange resin Amberlite® IRP64 was weighed and added to the mixer. The mixer was closed, stirred at high speed for 5 minutes, opened and scraped down, if necessary. Finally, the mixer was stirred for further 5 minutes at high speed.

Thereby, a mixture of nicotine and cation exchange resin was produced from the constituents stated in the below table 4D.

TABLE 4D

Ingredients used to manufacture nicotine premix V.

| Constituent | Amount (kg) | Amount (%) |
|---|---|---|
| Nicotine | 5.15 | 39.8 |
| Water | 2.80 | 21.6 |
| Resin | 4.32 | 33.4 |
| Pea fiber | 0.67 | 5.2 |
| Total | 12.94 | 100.0 |

Nicotine:resin ratio: 1.19:1 (1.19)
% water in obtained nicotine-resin composition: 21.6
The total process time was 20 minutes.

Example 3A—Pouches

Pouches PPC6-PPC7 containing nicotine polacrilex resin (NPR) or nicotine bitartrate (NBT) are prepared comprising powdered compositions as outlined in table 5. The pouches are made as follows.

Fibers and water are mixed using a planetary Bear Varimixer mixer for 5 minutes. Then, the following ingredients were added subsequently under continuous mixing: first Nicotine bitartrate xH2O (NBT, nicotine content of 32.5%) or nicotine polacrilex resin (NPR, nicotine content of 15.9%) as applicable (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch membrane of example 1A, made from long fiber paper, is used. The powder is filled into pouches and is maintained in the pouch by a sealing. Pouched products using the pouch membrane of example 1B were also made.

The powder is filled into pouches and is maintained in the pouch by a sealing.

Pouches PPC1-PPC5 containing nicotine premix are prepared comprising powdered compositions as outlined in table 5. The pouches are made as follows.

Fibers and water are mixed using a planetary Bear Varimixer mixer for 5 minutes. Then, the following ingredients were added subsequently under continuous mixing: Nicotine premix (mixed for 2 minutes), then the remaining ingredients except liquid flavor and glidant if any (mixed for 2 minutes), then liquid flavor if any (mixed for 1 minute), then glidant if any (mixed for 1 minute). The total mixing time is 9-11 minutes.

The final powder composition is filled into pouches (target fill weight 500 mg powder per pouch). The pouch membrane of example 1A, made from long fiber paper, is used. The powder is filled into pouches and is maintained in the pouch by a sealing. Pouched products using the pouch membrane of example 1B were also made.

The powder is filled into pouches and is maintained in the pouch by a sealing.

TABLE 5

The nicotine premix II (example 2B) comprises 34.1 wt % water, thereby contributing to the total water content.

| PPC | PPC1 | PPC2 | PPC3 | PPC5 | PPC6 | PPC7 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 25 | 15 | 40 | 30 | 30 |
| Raw material | Content in weight percent | | | | | |
| NPR | — | — | — | — | — | 12.1 |
| NBT | — | — | — | — | 5.9 | — |
| Nicotine premix II | 14.6 | 14.6 | 14.6 | 14.6 | — | — |
| Xylitol DC | 11.3 | 16.3 | 26.3 | 1.3 | 15.0 | 8.8 |
| Purified water | 25 | 20 | 10 | 35 | 30 | 30 |
| Wheat fiber | 30 | 30 | 30 | 30 | 30 | 30 |
| Sodium aliginate | 2.0 | 2.0 | 2.0 | 2.0 | 2.0 | 2.0 |
| Sodium carbonate | 5.0 | 5.0 | 5.0 | 5.0 | 5.0 | 5.0 |
| Flavor | 8.9 | 8.9 | 8.9 | 8.9 | 8.9 | 8.9 |
| NaCl | 0.1 | 0.1 | 0.1 | 0.1 | 0.1 | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

Pouch content: 500 mg total, i.e. nicotine conc 19.2 mg/g

The Xylitol DC applied is e.g. trade name "Xylitab 200".

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC1-PPC3, PPC5 show that different pouches having a water content of at least 15% by weight of the pouch composition can be made using free-base nicotine. Pouches PPC6-PPC7 have a similar water content as PPC1, but uses nicotine salt and nicotine in complex with an ion exchange resin.

Example 3B—Pouches

Pouches PPC11-PPC15 are made similarly to pouches PPC1-PPC5 of example 3A. Pouches PPC11-PPC15 containing nicotine premix are prepared comprising powdered compositions as outlined in table 6. The pouches are made as follows.

Fibers and powder ingredients (except glidants) are mixed using a planetary Bear Varimixer mixer for 2 minutes. Then, Nicotine premix is added and mixed for 2 minutes. Water is then added and mixed for 5 minutes followed by liquid flavor (if any—mixed for 1 minute) and glidant (if any—mixed for 1 minute). The total mixing time is 9-11 minutes.

TABLE 6

The nicotine premix II comprises 34.1 wt % water, thereby contributing to the total water content.

| PPC | PPC11 | PPC12 | PPC13 | PPC15 |
|---|---|---|---|---|
| Amount of nicotine | 9.6 mg | 9.6 mg | 9.6 mg | 9.6 mg |
| Water content [wt %] | 30 | 25 | 15 | 35 |
| Raw material | Content in weight percent | | | |
| Nicotine premix II | 14.6 | 14.6 | 14.6 | 14.6 |
| Isomalt DC | 11.3 | 22.3 | 44.3 | 0.3 |
| Purified water | 25 | 20 | 10 | 30 |
| Wheat fiber | 30 | 24 | 12 | 36 |
| Sodium alginate | 2.0 | 2.0 | 2.0 | 2.0 |
| Sodium carbonate | 5.0 | 5.0 | 5.0 | 5.0 |
| Flavor | 9.0 | 9.0 | 9.0 | 9.0 |
| High intensity sweetener | 1.0 | 1.0 | 1.0 | 1.0 |
| Potassium sorbate | 0.1 | 0.1 | 0.1 | 0.1 |
| Silicon dioxide | 2.0 | 2.0 | 2.0 | 2.0 |
| Total | 100 | 100 | 100 | 100 |

Pouch content: 500 mg total.

The applied Isomalt DC e.g. GalenIQ 720.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC11-PPC13, PPC15 shows varying water content of at least 15% by weight of the pouch composition. The water content varies, but the ratio between the amount of added purified water and the amount of fibers remain constant.

Example 3C—Pouches

Pouches PPC21-PPC25 are made similarly to pouches PPC11-PPC15 of example 3B.

TABLE 7

| PPC | PPC21 | PPC22 | PPC23 | PPC24 | PPC25 | PPC26 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |

TABLE 7-continued

| Raw material | Content in weight percent | | | | | |
|---|---|---|---|---|---|---|
| Nicotine premix II | 14.6 | 7.3 | 14.6 | 14.6 | 14.6 | 14.6 |
| Liquid nicotine* | — | 1.0 | — | — | — | — |
| Xylitol DC | 11.3 | 15.1 | 16.3 | 13.3 | 11.4 | 9.4 |
| Purified water | 25 | 27.5 | 25 | 25 | 25 | 25 |
| MCC (Avicel 102) | 30 | — | — | — | — | — |
| Wheat fiber | — | 30 | 30 | 30 | 30 | 30 |
| Sodium aliginate | 2.0 | 2.0 | 2.0 | 2.0 | 2.0 | 2.0 |
| Sodium carbonate | 5.0 | 5.0 | — | 3.0 | 5.0 | 7.0 |
| Flavor | 9.0 | 9.0 | 9.0 | 9.0 | 9.0 | 9.0 |
| High intensity sweetener | 1.0 | 1.0 | 1.0 | 1.0 | 1.0 | 1.0 |
| Potassium sorbate | 0.1 | 0.1 | 0.1 | 0.1 | — | — |
| Silicon dioxide | 2.0 | 2.0 | 2.0 | 2.0 | 2.0 | 2.0 |
| Total | 100 | 100 | 100 | 100 | 100 | 100 |

*Liquid nicotine is added as a nicotine-sugar alcohol premix in powder form.
The nicotine premix II comprises 34.1 wt % water, thereby contributing to the toal water content.

Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC21 shows the use of e.g. microcrystalline cellulose (MCC) instead of wheat fibers.

Pouch PPC22 shows the use of a combination of nicotine-ion exchange resin premix and nicotine-sugar alcohol premix.

Pouches PPC23-PPC26 shows the use of different amounts of buffering agent (here sodium carbonate). For high amounts of basic buffering agents, achieving a more alkaline environment, there is less need for a preservative (here potassium sorbate), therefore it is omitted in PPC25-PPC26, having the highest amounts of alkaline buffering agents.

Example 3D—Pouches

Pouches PPC31-PPC32 are made similarly to pouches PPC1-PPC5 of example 3A, but using nicotine premix I and III, respectively.

Pouches PPC31-PPC35 are made as described below.

The nicotine and sugar alcohol (xylitol, sorbitol, maltitol or other) are weighed. The nicotine is slowly added to the sugar alcohol powder under stirring (Kitchenaid mixer operated at about 30 RPM in about 30 minutes). The resulting granulate is sieved and placed on a tray. The resulting powder is dried at ambient temperature overnight and is thereafter sieved to obtain a nicotine-sugar alcohol premix. It is also possible to add an amount of water to the nicotine before mixing with the sugar alcohol. Any such water will then be evaporated during the drying.

Fibers and water are mixed using a planetary Bear Varimixer mixer for 5 minutes. Then, the following ingredients were added subsequently under continuous mixing: Powder ingredients other than nicotine premix (mixed for 2 minutes), nicotine-sugar alcohol premix (mixed for 2 minutes), then liquid flavor if any (mixed for 1 minute) and finally glidant if any (mixed for 1 minute). The total mixing time is 9-11 minutes.

The final powder composition is filled into pouches (target fill weight 500 mg powder per pouch). The pouch membrane of example 1A, made from long fiber paper, is used. The powder is filled into pouches and is maintained in the pouch by a sealing. Pouched products using the pouch membrane of example 1B were also made.

TABLE 8

| PPC | PPC31 | PPC32 | PPC33 | PPC34 | PPC35 | PPC36 | PPC37 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix I | 33.7 | — | — | — | — | — | — |
| Nicotine premix III | — | 10.4 | — | — | — | — | — |
| Liquid nicotine* | — | — | 1.9 | 1.9 | 1.9 | 1.9 | 1.9 |
| Isomalt DC | 11.2 | 11.3 | 19.0 | — | — | — | — |
| Sorbitol DC | — | — | — | 19.0 | — | — | — |
| Maltitol DC | — | — | — | — | 19.0 | — | — |
| Inulin | — | — | — | — | — | 19.0 | — |
| Polydextrose | — | — | — | — | — | — | 19.0 |
| Purified water | 6 | 29.2 | 30 | 30 | 30 | 30 | 30 |
| Wheat fiber | 30 | 30 | 30 | 30 | 30 | 30 | 30 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 9.0 | 9.0 | 9.0 | 9.0 | 9.0 | 9.0 | 9.0 |

TABLE 8-continued

| | | | | | | | |
|---|---|---|---|---|---|---|---|
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

*Liquid nicotine is added as a nicotine-sugar alcohol premix or a nicotine-water-soluble fiber premix in powder form.
The nicotine premix I comprises 71.4 wt % water, thereby contributing to the total water content.
The nicotine premix II comprises 34.1 wt % water, thereby contributing to the total water content.
The nicotine premix III comprises 7.5 wt % water, thereby contributing to the total water content.

Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC31-PPC32 show use of other nicotine premixes.

Pouches PPC33-PPC35 show use of nicotine pre-mixed with different sugar alcohol.

Pouches PPC36-PPC37 show use of nicotine pre-mixed with different water-soluble fibers.

Example 3E—Pouches

Pouches PPC41-PPC46 are made similarly to pouches PPC1-PPC5 of example 3A.

TABLE 9

The nicotine premix II comprises 34.1 wt % water, thereby contributing to the total water content.

| PPC | PPC41 | PPC42 | PPC43 | PPC44 | PPC45 | PPC46 |
|---|---|---|---|---|---|---|
| Amount of nicotine | 4.8 mg | 7.2 mg | 9.6 mg | 12 mg | 9.6 mg | 9.6 mg |
| Water content [wt %] | 27.5 | 28.3 | 30 | 31.2 | 30 | 30 |
| Raw material | Content in weight percent | | | | | |
| Nicotine premix II | 7.3 | 9.7 | 14.6 | 18.3 | 14.6 | 14.6 |
| Xylitol DC | 18.6 | 16.2 | 11.3 | 7.6 | 13.3 | 5 |
| Erythritol | — | — | — | — | — | 6.3 |
| Purified water | 25 | 25 | 25 | 25 | 25 | 25 |
| Wheat fiber | 30 | 30 | 30 | 30 | 30 | 30 |
| Sodium alginate | 2.0 | 2.0 | 2.0 | 2.0 | — | 2.0 |
| Sodium carbonate | 5.0 | 5.0 | 5.0 | 5.0 | 5.0 | 5.0 |
| Flavor | 9.0 | 9.0 | 9.0 | 9.0 | 9.0 | 8.9 |
| NaCl | — | — | — | — | — | 0.1 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouches PPC41-PPC44 show use of different doses of nicotine, from 4.8 mg to 12 mg.

Pouch PPC45 shows pouch without alginate, otherwise comparable to pouch PPC43.

Pouch PPC46 shows a pouch with a combination of two sugar alcohols.

Example 3F—Pouches

Pouches PPC51-PPC55 are made as follows.

Fibers and powder ingredients (except nicotine containing powders and glidants) are mixed for 1 minute using a planetary Bear Varimixer mixer. Then, NPR and NBT is added and mixed for 2 minutes (if applicable). Nicotine premix is then added and mixed for 2 minutes. Subsequently, water is added and mixed for 5 minutes followed by liquid flavor (if any—mixed for 1 minute) and glidant (if any—mixed for 1 minute). The total mixing time is 9-11 minutes.

The final powder composition is filled into pouches (target fill weight 500 mg powder per pouch). The pouch membrane of example 1A, made from long fiber paper, is used. The powder is filled into pouches and is maintained in the pouch by a sealing. Pouched products using the pouch membrane of example 1B were also made.

TABLE 10

The nicotine premix II comprises 34.1 wt % water, thereby contributing to the total water content. The nicotine premix VI comprises 27.5 wt % water, thereby contributing to the total water content.

| PPC | PPC51 | PPC52 | PPC53 | PPC54 | PPC55 |
|---|---|---|---|---|---|
| Amount of nicotine | 9.6 mg | 9.6 mg | 9.6 mg | 12 mg | 12 mg |
| Water content [wt %] | 30 | 30 | 30 | 30 | 30 |
| Raw material | Content in weight percent | | | | |
| NPR | – | 6.0 | 3.0 | – | – |
| NBT | 2.9 | – | 1.5 | 3.6 | – |
| Nicotine premix II | 7.3 | 7.3 | 7.3 | – | – |
| Nicotine premix VI | – | – | – | – | 8.0 |
| Isomalt DC | 15.2 | 12.1 | 13.6 | 19.3 | 17.1 |
| Purified water | 27.5 | 27.5 | 27.5 | 30.0 | 27.8 |
| Wheat fiber | 30 | 30 | 30 | 30 | 30 |
| Sodium carbonate | 5.0 | 5.0 | 5.0 | 5.0 | 5.0 |
| Flavor | 9.0 | 9.0 | 9.0 | 9.0 | 9.0 |
| High intensity sweetener | 1.0 | 1.0 | 1.0 | 1.0 | 1.0 |
| Potassium sorbate | 0.1 | 0.1 | 0.1 | 0.1 | 0.1 |
| Silicon dioxide | 2.0 | 2.0 | 2.0 | 2.0 | 2.0 |
| Total | 100 | 100 | 100 | 100 | 100 |

Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium carbonate is used as an alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium may as an example be used as high intensity sweeteners. Other usable high intensity sweeteners described herein may be used in combination with or instead of acesulfame potassium.

Pouch PPC51 shows pouch using nicotine-ion exchange resin premix in combination with nicotine bitartrate (NBT).

Pouch PPC52 shows pouch using nicotine-ion exchange resin premix in combination with nicotine polacrilex resin (NPR).

Pouch PPC53 shows pouch using nicotine-ion exchange resin premix in combination with nicotine bitartrate (NBT) and nicotine polacrilex resin (NPR).

Example 3G—Pouches

Pouches PPC61-PPC65 containing nicotine premix are prepared comprising powdered compositions as outlined in table 11. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

TABLE 11

The nicotine premix VI comprises 27.5 wt % water, thereby contributing to the total water content.

| PPC | PPC61 | PPC62 | PPC63 | PPC64 | PPC65 | PPC66 | PPC67 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix VI | 6.4 | 6.4 | 6.4 | 6.4 | 6.4 | 6.4 | 6.4 |
| Xylitol | 5 | 18.3 | 18.3 | 18.3 | 5 | 5 | 5 |
| Erythritol | 13.5 | — | — | — | 13.5 | 13.5 | 13.5 |
| Purified water | 28 | 28 | 28 | 28 | 28 | 28 | 28 |
| Wheat fiber | 30 | 30 | 20 | 40 | 30 | 30 | 30 |
| Sodium alginate | 2.0 | 2.0 | 2.0 | 2.0 | 2.0 | — | — |
| Glycerol | — | — | — | — | — | 2.0 | — |
| Hydroxy propyl cellulose | — | — | — | — | — | — | 2.0 |
| Sodium carbonate | 5.0 | 3.0 | 3.0 | 3.0 | 3.0 | 3.0 | 3.0 |
| Sodium bicarbonate | — | 2.0 | 2.0 | 2.0 | 2.0 | 2.0 | 2.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |

TABLE 11-continued

The nicotine premix VI comprises 27.5 wt % water, thereby contributing to the total water content.

| | | | | | | | |
|---|---|---|---|---|---|---|---|
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Pouch content: 500 mg total.

Wheat fiber, trade name "Vitacel 600 WF plus". Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, bamboo fibers, bran fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC61-PPC62 show use of different sweetener and buffer combinations.

Pouches PPC63-PPC64 show pouches with varying fiber content.

Pouches PPC65-PPC67 show use of different humectants.

Example 3H—Pouches

Pouches PPC71-PPC76 containing nicotine premix are prepared comprising powdered compositions as outlined in table 12. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 12

The nicotine premixes comprise water in varying amount, thereby contributing to the total water content.

| PPC | PPC71 | PPC72 | PPC73 | PPC74 | PPC75 | PPC 76 | PPC 77 |
|---|---|---|---|---|---|---|---|
| Amount of nicotine | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 |
| Raw material | Content in weight percent | | | | | | |
| Nicotine premix IV | 19.2 | — | — | — | — | — | — |
| Nicotine premix V | — | 9.6 | — | — | — | — | — |
| Nicotine premix VI | — | — | — | — | 6.4 | 6.4 | 6.4 |
| Nicotine premix VII | — | — | 4.6 | — | — | — | — |
| Nicotine premix VIII | — | — | — | 4.8 | — | — | — |
| Purified water | 21 | 27 | 29 | 29 | 28 | 28 | 28 |
| Wheat fiber | 30 | 30 | 30 | 29.75 | — | — | — |
| Oat fiber | — | — | — | — | 30 | — | — |
| Pea fiber | — | — | — | 0.25 | — | 30 | — |
| Powdered cellulose | — | — | — | — | — | — | 30 |
| Xylitol DC | 5.0 | 5.0 | 5.0 | 5.0 | 5.0 | 5.0 | 5.0 |
| Erythritol | 7.7 | 11.3 | 14.3 | 14.1 | 13.5 | 13.5 | 13.5 |
| Sodium alginate | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 |
| Total | 100 | 100 | 100 | 100 | 100 | 100 | 100 |

Nicotine premix VIII comprises peafiber.

Pouch content: 500 mg total, i.e. nicotine conc 19.2 mg/g

Wheat fiber, trade name "Vitacel 600 WF plus".

Powdered cellulose, trade name "Vitacel L00" or "Vitacel L700G".

Oat fiber, trade name "Vitacel HF 600".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, bamboo fibers, bran fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC71-PPC74 show use of different nicotine premixes.

Pouches PPC75-PPC77 show use of different fibers.

Example 3I—Pouches

Pouches PPC81-PPC92 containing nicotine premix are prepared comprising powdered compositions as outlined in table 13. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 13 I/II

| PPC | PPC81 | PPC82 | PPC83 | PPC84 | PPC85 | PPC86 | PPC87 | PPC88 |
|---|---|---|---|---|---|---|---|---|
| Amount of nicotine | 9.6 mg | 9.6 mg | 9.6 mg | 9.6 mg | 9.6 mg | 9.6 mg | 9.6 mg | 9.6 mg |
| Water content [wt %] | 30 | 30 | 30 | 30 | 30 | 30 | 30 | 30 |
| Raw material | Content in weight percent | | | | | | | |
| Nicotine premix II | 14.6 | 14.6 | 14.6 | 14.6 | — | — | — | — |
| Nicotine premix VI | — | — | — | — | 6.4 | 6.4 | 6.4 | 6.4 |
| Purified water | 25 | 25 | 25 | 25 | 28 | 28 | 28 | 28 |
| Wheat fiber | 30 | — | — | — | — | — | — | 15 |
| Oat fiber | — | 30 | — | — | 15 | — | — | — |
| Pea fiber | — | — | 30 | — | — | 15 | — | — |
| Powdered cellulose | — | — | — | 30 | — | — | 15 | — |
| Xylitol DC | 5.0 | 5.0 | 5.0 | 5.0 | 5.0 | 5.0 | 5.0 | 5.0 |
| Erythritol | 8.3 | 8.3 | 8.3 | 8.3 | 28.5 | 28.5 | 28.5 | 28.5 |
| Sodium alginate | 2.0 | 2.0 | 2.0 | 2.0 | 2.0 | 2.0 | 2.0 | 2.0 |
| Sodium carbonate | 5.0 | 5.0 | 5.0 | 5.0 | 5.0 | 5.0 | 5.0 | 5.0 |
| Flavor | 7.0 | 7.0 | 7.0 | 7.0 | 7.0 | 7.0 | 7.0 | 7.0 |
| High intensity sweetener | 1.0 | 1.0 | 1.0 | 1.0 | 1.0 | 1.0 | 1.0 | 1.0 |
| Potassium sorbate | 0.1 | 0.1 | 0.1 | 0.1 | 0.1 | 0.1 | 0.1 | 0.1 |
| Silicon dioxide | 2.0 | 2.0 | 2.0 | 2.0 | 2.0 | 2.0 | 2.0 | 2.0 |
| Total | 100 | 100 | 100 | 100 | 100 | 100 | 100 | 100 |

TABLE 13 II/II

| PPC | PPC 89 | PPC 90 | PPC 91 | PPC 92 | PPC 93 | PPC 94 |
|---|---|---|---|---|---|---|
| Amount of nicotine | 9.6 mg | 9.6 mg | 9.6 mg | 9.6 mg | 9.6 mg | 9.6 mg |
| Water content [wt %] | 30 | 30 | 30 | 30 | 30 | 30 |
| Raw material | Content in weight percent | | | | | |
| Nicotine premix II | 14.6 | 14.6 | 14.6 | 14.6 | | |

TABLE 13 II/II-continued

| | | | | | | |
|---|---|---|---|---|---|---|
| Nicotine premix VI | — | — | — | — | 6.4 | 6.4 |
| Purified water | 25 | 25 | 25 | 25 | 28 | 28 |
| Wheat fiber | 15 | — | — | — | 15 | 15 |
| Oat fiber | — | 15 | — | — | — | — |
| Pea fiber | — | — | 15 | — | — | — |
| Powdered cellulose | — | — | — | 15 | — | — |
| Xylitol DC | 5.0 | 5.0 | 5.0 | 5.0 | 5.0 | 5.0 |
| Erythritol | 23.3 | 23.3 | 23.3 | 23.3 | 28.5 | 20.5 |
| Sodium alginate | 2.0 | 2.0 | 2.0 | 2.0 | — | — |
| NaCl | — | — | — | — | — | 10 |
| Sodium carbonate | 5.0 | 5.0 | 5.0 | 5.0 | 3.5 | 5.0 |
| Sodium bicarbonate | — | — | — | — | 3.5 | — |
| Flavor | 7.0 | 7.0 | 7.0 | 7.0 | 7.0 | 7.0 |
| High intensity sweetener | 1.0 | 1.0 | 1.0 | 1.0 | 1.0 | 1.0 |
| Potassium sorbate | 0.1 | 0.1 | 0.1 | 0.1 | 0.1 | 0.1 |
| Silicon dioxide | 2.0 | 2.0 | 2.0 | 2.0 | 2.0 | 2.0 |
| Total | 100 | 100 | 100 | 100 | 100 | 100 |

The nicotine premixes comprise water in varying amount, thereby contributing to the total water content.

Pouch content: 500 mg total, i.e. nicotine conc 19.2 mg/g

Wheat fiber, trade name "Vitacel 600 WF plus" or "Vitacel 200WF".

Powdered cellulose, trade name "Vitacel L00" or "Vitacel L700G".

Oat fiber, trade name "Vitacel HF 600".

Pea fiber, trade name "Vitacel EF150".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, bamboo fibers, bran fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Pouches PPC81-PPC92 shows the use of different fibers, in different amounts and with different nicotine premixes.

Pouches PPC93-PPC94 show use of buffer pair and higher amount of salt, respectively.

Example 3J—Pouches

Pouches Comp. 10, PPC101, PPC102 containing nicotine premix are prepared comprising powdered compositions as outlined in table 14. The pouches are made as follows.

Fibers and powder ingredients (except glidants) are mixed using a Lödige mixer for 2 minutes. Then, Nicotine premix is added and mixed for 2 minutes. With the mixer running, water is then added during a period of 15 minutes followed by liquid flavor (if any—mixed for 15 minutes) and glidant (if any—mixed for 1 minute). The total mixing time is 19-35 minutes.

The final powder composition is filled into pouches (target fill weight 500 mg powder per pouch). The pouch material of example 1, made from long fiber paper, is used. The powder is filled into pouches and is maintained in the pouch by a sealing.

TABLE 14

The nicotine premix II comprises 34.1 wt % water, thereby contributing to the total water content.

| PPC | Comp. 10 | PPC101 | PPC102 |
|---|---|---|---|
| Amount of nicotine | 9.6 mg | 9.6 mg | 9.6 mg |
| Water content [wt %] | 5 | 15 | 45 |
| Raw material | Content in weight percent | | |
| Erythritol | 7.2 | 7.2 | 5.0 |
| Xylitol | 5 | 5.0 | 0.0 |
| Nicotine premix II | 14.6 | 14.6 | 14.6 |
| Sodium carbonat | 4 | 4.0 | 4.0 |
| High intensity sweetener | 1.1 | 1.1 | 1.0 |
| Sodium alginate | 2 | 2.0 | 2.0 |
| Wheat fiber | 55 | 45.0 | 27.0 |
| Purified water | 0 | 10.0 | 40.0 |
| Sodium chloride | 0.1 | 0.1 | 0.2 |
| Potassium sorbate | 0.1 | 0.1 | 0.2 |
| Silicon dioxide | 2 | 2.0 | 2.0 |
| Flavor | 8.9 | 8.9 | 4.1 |
| Total | 100 | 100 | 100 |

The nicotine premixes comprise water in varying amount, thereby contributing to the total water content.

Pouch content: 500 mg total, i.e. nicotine conc 19.2 mg/g

Wheat fiber, trade name "Vitacel 600 WF plus" or "Vitacel 200WF".

Other fibers may be used as well, such as water-insoluble plant fibers, such as oat fibers, pea fibers, rice fiber, maize fibers, oat fibers, tomato fibers, barley fibers, rye fibers, sugar beet fibers, buckwheat fibers, potato fibers, apple fibers, cocoa fibers, bamboo fibers, bran fibers, and powdered cellulose.

For example, a mixture of e.g. menthol and peppermint may be used. Of course, other flavors as described herein may be use as well, in combination with menthol and/or peppermint or replacing these.

Silicon dioxide is used as a glidant. Other possible glidants include e.g. magnesium stearate, starch and talc.

Sodium alginate, glycerol and hydroxypropyl cellulose (HPC) may be used as humectants. Other humectants as described herein may also be used in combination with sodium alginate, glycerol or HPC or as an alternative.

Sodium carbonate and sodium bicarbonate are used as alkaline buffering agent. Other buffering agents as described herein may also be used in combination with sodium carbonate or an alternative.

Potassium sorbate is used as a preservative. Other preservatives as described herein may also be used in combination with or instead of potassium sorbate.

Acesulfame potassium and/or sucralose may as an example be used as high intensity sweeteners. Other usable high intensity sweeteners described herein may be used in combination with or instead of acesulfame potassium and/or sucralose.

Example 4A—Processing of Nicotine into the Pouch Membrane

The nicotine pouch was positioned at a temperature of about 25 degrees Celsius in a closed processing container. The temperature of the nicotine pouch was kept constant for a period of 14 days, while maintaining the container in a closed condition.

After 14 days processing, the container was opened, and the pouch membrane and the pouch composition were examined for nicotine content.

Example 4B—Applying Nicotine to the Pouch Membrane

The pouched product was soaked in liquid nicotine (diluted in propylenglycol to a nicotine concentration of about 20%) to apply the nicotine on the pouch membrane.

The soaking process was continued for about 5 minutes.

Thereafter, the pouch membrane and the pouch composition were examined for nicotine content.

Example 4C—Applying Nicotine by Spraying

A liquid nicotine solution (diluted in propylenglycol to a nicotine concentration of to about 20%) was applied by spraying on the pouched product.

Subsequently, the pouched product was allowed to dry for about 10 minutes at ambient conditions.

Thereafter, the pouch membrane and the pouch composition were examined for nicotine content.

Example 4D—Pouch Membranes

Pouched products were made using pouch composition PPC55 using different pouch membranes. PPC55-A was made with a pouch membrane having fibers consisting essentially of regenerated cellulose (viscose) and processed according to example 4A. PPC55-B was made with a pouch membrane having fibers being a combination of regenerated cellulose (viscose) and synthetic fibers, and processed according to example 4A. PPC55-C was made with a pouch membrane having fibers being a combination of viscose and synthetic fiber material and processed according to example 4A. The pouch membrane fiber composition of PPC55-C differed from that of PPC55-B with PPC55-C having a slightly more dense composition.

Example 5A—Processing of Nicotine into the Pouch Membrane

Pouched product made according to example 4A using the pouch composition PPC44 of example 3E. The obtained pouched product was tested for nicotine content in the pouch membrane. Of the about 12 mg of total nicotine content in the pouched product added to the pouch composition during manufacturing, the processed pouched product contained about 8.5 mg nicotine in the pouch composition and about 3.5 mg nicotine in the pouch membrane, corresponding to about 29% by weight of the total amount of nicotine. The pouch membrane had a weight corresponding to about 12% by weight of the pouched product when making the pouched product.

Example 5B—Release of Nicotine

The pouch composition and the pouch membrane of the processed pouch PPC44 in example 5A was then tested separately to evaluate nicotine release. It was observed that the pouch composition itself (without the pouch membrane) released about 40% by weight of its nicotine content at time point 10 min. in an in vitro experiment in accordance with example 5F. The pouch membrane itself released about 92% of its weight at time point 10 min. when applied to a corresponding test. This confirms that the nicotine of the pouch membrane releases considerably faster and more effective than the nicotine of the pouch composition.

Example 5C—Processing Time

Pouched products according to PPC44, PPC54, and PPC55 were processed in accordance with example 4A. At times 0, 1, 4, and 7 days after initiation of the processing, a pouched product of each of PPC44, PPC54, and PPC55 was tested for content of nicotine in the pouch membrane. Results are shown in table 15.

TABLE 15

Nicotine content of pouch membranes.

| | Processing time [days] | | | |
|---|---|---|---|---|
| | 0 | 1 | 4 | 7 |
| | Nicotine amount in % by weight of the total amount of nicotine | | | |
| PPC44 | 5.6 | 10.7 | 12.2 | 15.3 |
| PPC54 | 6.4 | 19.7 | 30.2 | 30.9 |
| PPC55 | 5.8 | 22.1 | 27.5 | 35.3 |

As can be seen from table 15, the amount of nicotine in the pouch membrane may be varied by adjusting the nicotine source and also by adjusting the processing time. A longer processing time results in a higher amount of nicotine in the pouch membrane. Also, exchanging nicotine premix II (PPC44) with nicotine premix VI (PPC55) results in a markedly faster and more efficient processing of nicotine into the pouch membrane.

Example 5D—Release from Pouched Products

Similarly, at times 0, 1, 4, and 7 days after initiation of the processing, in vitro release from a pouched product of each of PPC44, PPC54, and PPC55 was tested. Results of the nicotine release at time point 10 min. from the pouched products are shown in table 16.

TABLE 16

Residue amount of nicotine in the pouched products.

| | Processing time [days] | | | |
|---|---|---|---|---|
| | 0 | 1 | 4 | 7 |
| | Residue amount of nicotine % by weight of the initial amount | | | |
| PPC44 | 81 | 77 | 75 | 71 |
| PPC54 | 78 | 66 | 56 | 51 |
| PPC55 | 70 | 67 | 56 | 52 |

As shown in table 16, the processing of nicotine into the pouch membrane clearly leads to a more effective release of nicotine from the pouched product. At increasing processing time, more nicotine is processed into the pouch membrane. Since a remarkably high degree of release from the pouch membrane is demonstrated, e.g. 92% as shown above, increasing amount of nicotine in the pouch membrane by the processing leads to a more effective release of nicotine from the pouched products.

Example 5E—Release Test (in Vivo)

The release properties of the pouches were evaluated by a panel of assessors, preferably at least 8 assessors. Each assessors was provided with a pouch to place in the oral cavity, specifically at the upper lip.

Pouch was removed from the oral cavity of the test person after 2 min., 5 min., 10 min., 30 min. or 60 min.

The amount of remaining nicotine in the pouches were determined by standard HPLC techniques.

Two pouches were tested by each assessor for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 5F—Release Test (in Vitro)

The release properties of the pouches were tested in an in vitro experiment.

Individual pouches were put into reaction tubes containing 10 mL of 0.02 M potassium dihydrogen phosphate-buffer (pH adjusted to 7.4), temperature T=37 degrees C.

No stirring or shaken was applied during the release experiment.

Pouches were removed from the buffer after 2 min., 5 min., 10 min., 30 min. or 60 min. The wet pouch was allowed to drip off, where after the pouch was gently pulled over the edge of the reaction tube to remove any excess buffer associated with the wet pouch.

The amount of remaining nicotine in the pouches were determined by standard HPLC techniques.

Two pouches were tested for each timepoint. The average of the result obtained for each timepoint was used to make profiles of the nicotine content in the pouches over time.

The amount of released nicotine could thereafter be obtained by subtracting the remaining amount of nicotine in the pouch from the initial dosage of nicotine in the tested pouch.

Example 5H—Release from Pouches with Different Pouch Membranes

Release of nicotine from pouched products PPC55-A, PPC55-B, and PPC55-C according to example 4D were tested according to the method of example 5F. Results are shown in table 17.

TABLE 17

Nicotine in vitro release from pouched products

| Time [minutes] | PPC55-A | PPC55-B | PPC55-C |
| --- | --- | --- | --- |
| | Percentage of nicotine of the pouched product released | | |
| 0 | 0 | 0 | 0 |
| 2 | 29.92 | 12.10 | 15.87 |
| 5 | 36.76 | 33.20 | 22.16 |

TABLE 17-continued

Nicotine in vitro release from pouched products

| Time [minutes] | PPC55-A | PPC55-B | PPC55-C |
| --- | --- | --- | --- |
| 10 | 44.64 | 33.13 | 34.27 |
| 30 | 63.81 | 57.34 | 60.67 |

The pouches PPC55-A, PPC55-B, and PPC55-C were also tested for nicotine content in the pouch membrane prior to the release test. Pouch membrane of pouched product PPC55-A had a nicotine content of 22.4% by weight of the total content of nicotine in the pouched product. Pouch membrane of pouched product PPC55-B had a nicotine content of 19.0% by weight of the total content of nicotine in the pouched product. Pouch membrane of pouched product PPC55-C had a nicotine content of 29.7% by weight of the total content of nicotine in the pouched product.

The above results show that the pouch membrane material influences both the amount of nicotine that is processable into the pouch membrane, and further the release of nicotine during testing. Particularly, it shows that when using a viscose-based pouch membrane (i.e. a pouch membrane having fibers consisting essentially of viscose, PPC55-A), considerably higher release results were obtained, particularly at the earliest time point, compared to when the pouch membrane included both fibers of viscose and synthetic fibers (PPC55-B and PPC55-C).

Example 5I—Content of Nicotine in Pouch Membranes

The nicotine content in pouch membranes of pouched products Comp. 10, PPC101, and PPC102, processed according to example 4A at a reduced time period, was determined. The test was made after one day of processing, and average results are shown in table 18.

TABLE 18

Nicotine content in pouch membrane compared to the total content of nicotine in the pouched product for pouched products with varying water content.

| | Comp. 10 | PPC101 | PPC102 |
| --- | --- | --- | --- |
| Water content in pouch composition [wt %] | 5 | 15 | 45 |
| Nicotine content in pouch membrane [wt % of total nicotine content] | 0.8 | 2.9 | 18.4 |

The results of table 18 demonstrates that having a high water content in the pouch composition facilitates an effective processing of nicotine into the pouch membrane.

The test results of PPC101 showed a significant increase in nicotine content in the pouch membrane between early measurements, indicating that full processing was not yet obtained. Example 4A indicates a processing period of 14 days until the desired level of nicotine in the membrane is obtained. The processing time may nevertheless depend heavily e.g. on the amount of water.

The invention claimed is:
1. A nicotine pouched product comprising
a pouch composition and
a pouch membrane enclosing the pouch composition, the pouch composition comprising
at least one water-insoluble fiber,
water in an amount of at least 15% by weight of the composition, and nicotine,
wherein the pouch membrane comprises further nicotine in an amount of at least 15% by weight of a total content of nicotine in the pouched product.

2. The nicotine pouched product according to claim 1, wherein said at least one water-insoluble fiber is provided as a powder and wherein said pouch membrane comprises at least one further water-insoluble fiber.

3. The nicotine pouched product according to claim 1, wherein at least 15% by weight of said total content of nicotine in the pouched product is released within a period of no more than 120 seconds upon oral administration.

4. The nicotine pouched product according to claim 1, wherein the nicotine of the pouched product is selected from nicotine salts, free-base nicotine mixed with ion exchange resin, nicotine in complex with ion exchange resin, free-base nicotine mixed with a water-soluble composition such as sugar alcohol or water-soluble fiber, nicotine in association with a fatty acid and any combinations thereof.

5. The nicotine pouched product according to claim 1, wherein the pouch composition comprises sugar alcohol.

6. The nicotine pouched product according to claim 1, wherein the pouch composition comprises sugar alcohol in an amount of at least 1% by weight of the composition.

7. The nicotine pouched product according to claim 5, wherein said sugar alcohol is selected from the group consisting of sorbitol, erythritol, xylitol, lactitol, maltitol, mannitol, hydrogenated starch hydrolyzates, isomalt, or any combination thereof.

8. The nicotine pouched product according to claim 1, wherein the pouched product comprises said pouch membrane in an amount of 3-20 percent by weight of said pouched product.

9. The nicotine pouched product according to claim 1, wherein the pouch membrane comprises a non-woven material or a woven material.

10. The nicotine pouched product according to claim 1, wherein the pouch membrane comprises fibers, the fibers of the pouch membrane comprising cellulose in an amount of at least 60% by weight of the fibers.

11. The nicotine pouched product according to claim 1, wherein the amount of nicotine located in the pouch membrane is 15-50% by weight of said total content of nicotine in the pouched product.

12. The nicotine pouched product according to claim 1, wherein the further nicotine in the pouch membrane is provided by processing nicotine from the pouch composition into the pouch membrane.

13. The nicotine pouched product according to claim 1, wherein the further nicotine in the pouch membrane is applied to the pouch membrane by film coating or spraying.

14. The nicotine pouched product according to claim 1, wherein the further nicotine in the pouch membrane is applied to the pouch membrane by soaking the pouched product in liquid nicotine.

15. The nicotine pouched product according to claim 1, wherein the further nicotine is applied to the pouch membrane during manufacturing of said pouch membrane.

16. The nicotine pouched product according to claim 1, wherein the nicotine in the pouch composition is the same form as the further nicotine in the pouch membrane.

17. The nicotine pouched product according to claim 1, wherein the water-insoluble fiber of the pouch composition is selected from water-insoluble plant fibers, wheat fibers, pea fibers, rice fibers, maize fibers, oat fibers, tomato fibers, barley fibers, rye fibers, sugar beet fibers, buckwheat fibers, potato fibers, apple fibers, cocoa fibers, bamboo fibers, bran fibers, powdered cellulose, and any combination thereof.

18. The nicotine pouched product according to claim 1, wherein the pouch composition has a water content of 15 to 70% by weight of said pouch composition.

19. The nicotine pouched product according to claim 2, wherein both the water insoluble fibers of the membrane and the water-insoluble fibers of the pouch composition comprise natural fibers.

20. A nicotine pouched product comprising
a pouch composition and
a pouch membrane enclosing the pouch composition,
the pouch composition comprising
at least one water-insoluble fiber,
water in an amount of at least 15% by weight of the composition and nicotine,
wherein the pouch membrane further comprises at least 1.0 mg nicotine.

* * * * *